US011333652B2

United States Patent
Gotor et al.

(10) Patent No.: US 11,333,652 B2
(45) Date of Patent: May 17, 2022

(54) DETECTION OF ADULTERATED GASOLINE USING AN ENVIRONMENTALLY SENSITIVE PHOTOLUMINESCENT MOLECULAR PROBE

(71) Applicant: Bundesrepublik Deutschland, vertreten durch die Bundesministerin für Wirtschaft und Energie, Berlin (DE)

(72) Inventors: Raúl Gotor, Berlin (DE); Jérémy Bell, Berlin (DE); Knut Rurack, Berlin (DE)

(73) Assignee: Bundesrepublik Deutschland, vertreten durch die Bundesministerin für Energie Wirtschaft und Energie, Berlin (DE)

( * ) Notice: Subject to any disclaimer, the term of this patent is extended or adjusted under 35 U.S.C. 154(b) by 94 days.

(21) Appl. No.: 16/650,406

(22) PCT Filed: Sep. 29, 2017

(86) PCT No.: PCT/EP2017/074882
§ 371 (c)(1),
(2) Date: Mar. 25, 2020

(87) PCT Pub. No.: WO2019/063102
PCT Pub. Date: Apr. 4, 2019

(65) Prior Publication Data
US 2020/0225208 A1    Jul. 16, 2020

(51) Int. Cl.
*G01N 33/28* (2006.01)
*G01N 21/64* (2006.01)
(Continued)

(52) U.S. Cl.
CPC ..... *G01N 33/2882* (2013.01); *G01N 21/6428* (2013.01); *G01N 21/78* (2013.01);
(Continued)

(58) Field of Classification Search
CPC .. G01N 33/2882; G01N 21/78; G01N 33/225; G01N 33/2835; G01N 21/6428;
(Continued)

(56) References Cited

U.S. PATENT DOCUMENTS 5,591,400 A * 1/1997 Dektar ................... G01N 21/75
427/163.2
5,843,783 A    12/1998 Roginski et al.

FOREIGN PATENT DOCUMENTS

KR    20120031035 A *  3/2012
WO    9900666 A1     1/1999
(Continued)

OTHER PUBLICATIONS

Cvejn, et al., "Solvent and branching effect on the two-photon absorption properties of push-pull triphenylamine derivatives", Jan. 2016, RSC Advances, 6, 12819-12828. (Year: 2016).*
(Continued)

*Primary Examiner* — Samuel P Siefke
*Assistant Examiner* — Henry H Nguyen
(74) *Attorney, Agent, or Firm* — Bachman and Lapointe PC; George Coury

(57) ABSTRACT

A method for the detection of adulterated gasoline in a sample is disclosed. The method includes contacting a sample with an immobilized molecular probe, the immobilized molecular probe having a photoluminescence which is environmentally sensitive; collecting the photoluminescence from the immobilized molecular probe; and determining whether the photoluminescence is indicative of adulterated gasoline. A test strip for the detection of adulterated gasoline in a sample is also disclosed, including an immobilized molecular probe embedded in a substrate and/or immobilized to the substrate, the immobilized molecular probe having photoluminescence which is environmentally
(Continued)

sensitive to adulterated gasoline. The method and test strips are designed to be robust, portable, and within the capabilities of untrained personnel.

14 Claims, 7 Drawing Sheets

(51) Int. Cl.
  *G01N 21/78* (2006.01)
  *G01N 33/22* (2006.01)
  *G01N 21/77* (2006.01)
(52) U.S. Cl.
  CPC ....... *G01N 33/225* (2013.01); *G01N 33/2835* (2013.01); *G01N 2021/6439* (2013.01); *G01N 2021/7769* (2013.01); *G01N 2201/0221* (2013.01); *G01N 2201/127* (2013.01)
(58) Field of Classification Search
  CPC ... G01N 2021/7769; G01N 2021/6439; G01N 2201/0221; G01N 2201/127; G01N 31/22
  See application file for complete search history.

(56) References Cited

FOREIGN PATENT DOCUMENTS

| WO | 2006127840 A2 | 11/2006 |
| WO | 2014160212 A1 | 10/2014 |
| WO | 2017019337 A1 | 2/2017 |

OTHER PUBLICATIONS

Translation of KR20120031035A, Kim, Jong Man, Mar. 29, 2012 (Year: 2012).*

Kulathunga et al., "Fingerprinting diesel and petrol fuels for adulteration in Sri Lanka", J. National Sci. Foundation Sri Lanka 2013 41 (4): pp. 287-292.

Haidekker et al., "Ratiometric mechanosensitive fluorescent dyes: design and applications"., Journal of Materials Chemistry C, 2016, 4, pp. 2707-2718.

Lee et al., "Detection of adulterated gasoline using colorimetric organic microfibers", Journal of Materials Chemistry, 2011, 21, pp. 2648-2655.

* cited by examiner

| Dyes | 1 | | | | 2 | | | |
|---|---|---|---|---|---|---|---|---|
| Solvent | $\lambda_{abs}$ / nm | $\lambda_{em}$ / nm | Stokes shift / cm$^{-1}$ | $\varphi_F$ | $\lambda_{abs}$ / nm | $\lambda_{em}$ / nm | Stokes shift / cm$^{-1}$ | $\varphi_F$ |
| n-Hexane | 380 | 401 | 1378 | 0.66 | 382 | 406 | 1547 | 0.45 |
| Toluene | 381 | 432 | 3099 | 0.95 | 385 | 436 | 3038 | 0.790 |
| CHCl$_3$ | 384 | 472 | | 0.99 | 386 | 475 | 4854 | 0.99 |
| EtOH | 375 | 515 | 7249 | 0.78 | 379 | 521 | 7191 | 0.57 |
| MeCN | 372 | 543 | 8466 | 0.58 | 375 | 549 | 8452 | 0.37 |
| Gasoline | 379 | 430 | 3129 | 0.77 | 387 | 435 | 2851 | 0.69 |
| Kerosene | 384 | 406 | 1411 | 0.706 | 388 | 411 | 1442 | 0.714 |

DETECTION OF ADULTERATED GASOLINE USING AN ENVIRONMENTALLY SENSITIVE PHOTOLUMINESCENT MOLECULAR PROBE

FIELD AND BACKGROUND

The present invention relates to the detection of adulterated gasoline, such as with the use of a mobile communication and computing device or smartphone.

Adulteration of gasoline is a recurrent worldwide problem, especially in regions without strong regulations or powerful control agencies. The widespread use of gasoline makes it a target of nefarious and/or illegal practices mainly for economic reasons. Indeed, gasoline dilution can be achieved using cheap and less taxed solvents of similar composition such as mineral spirits, kerosene, rubber solvent, petrochemical naphtha, diesel and thinner, but also an excessive amount of ethanol. Detection of adulterated gasoline using expensive and complex equipment by experts in a laboratory environment is possible. A simple means of detection using samples on site, for example, at petrol stations is desirable.

SUMMARY

Against this background, disclosed herein is a method for detection of adulterated gasoline in a sample, making use of an immobilized molecular probe which has an environmentally sensitive photoluminescence. In some embodiments, the probe is immobilized to a test strip. Disclosed herein is a method and a test strip. Further configurations, details, and features of the present invention are also described herein.

Herein is disclosed a method for detection of an adulterated gasoline in a sample. The method includes contacting a sample with a molecular probe, the molecular probe having a photoluminescence which is environmentally sensitive. The photoluminescence from the molecular probe is collected. The method includes determining whether the photoluminescence is indicative of adulterated gasoline. The disclosed method provides a rapid, portable, and inexpensive analysis that does not require extensive training to perform.

According to a further embodiment, which can be combined with any other embodiment disclosed herein, the immobilized molecular probe is environmentally sensitive to polarity. A polarity sensitive immobilized molecular probe may be particularly sensitive to gasoline adulterations that affect the polarity, for example, alcohols such as ethanol can significantly affect the polarity of adulterated gasoline.

According to a further embodiment, which can be combined with any other embodiment disclosed herein, the immobilized molecular probe has a polar excited state, the immobilized molecular probe optionally being a charge transfer dye. Without being bound by theory, an immobilized molecular probe with a polar excited state may be particularly sensitive to polarity changes of adulterated gasoline.

According to a further embodiment, which can be combined with any other embodiment disclosed herein, the immobilized molecular probe is covalently immobilized to a substrate, the molecular probe covalently bound to the substrate optionally through a spacer group. A spacer group may allow for the immobilized molecular probe to make better contact with the sample and may increase the sensitivity of the immobilized molecular probe to the sample.

According to a further embodiment, which can be combined with any other embodiment disclosed herein, the immobilized molecular probe comprises a donor and an acceptor which are covalently bound to each other, such as via a conjugated linker such as a phenylacetylene; for example, the immobilized molecular probe includes a triphenylamino moiety as the donor and a cyano group as the acceptor; particularly,

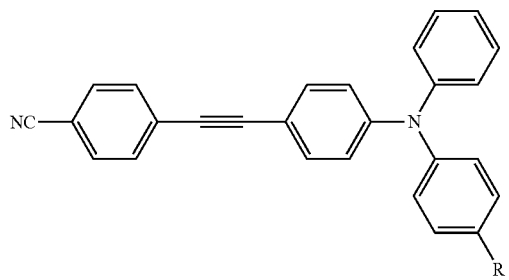

wherein R is selected from H,

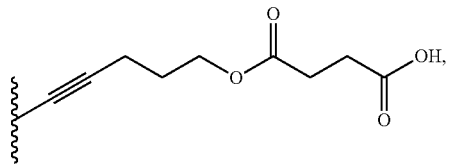 [SMILES: *C#CCCCOC(=O)CCC(=O)O]

and a species immobilizing the immobilized molecular probe to a substrate.

Donor acceptor pairs may be particularly sensitive to the presence of adulterated gasoline. They may have significant charge redistribution upon excitation, which may make the photoluminescence sensitive to polarity of the environment, for example.

According to a further embodiment, which can be combined with any other embodiment disclosed herein, the immobilized molecular probe is formed from a molecular probe which includes a functional group for covalently immobilizing the molecular probe to a substrate, the functional group being, for example, an alkoxyl, thiol, sulfoxide, alkyl halide, primary or secondary amine, carboxylic acid, isothiocyanate, epoxide, azide, alkyne, phosphate or phosphoryl group, aldehyde, N-succinimidyl ester, or maleimide. The immobilized molecular probe can include a spacer group for reducing the interaction of the substrate with the molecular probe, such as an interaction which sterically hinders the sample from contacting the immobilized molecular probe.

According to a further embodiment, which can be combined with any other embodiment disclosed herein, the immobilized molecular probe may be formed from a molecular probe of the form

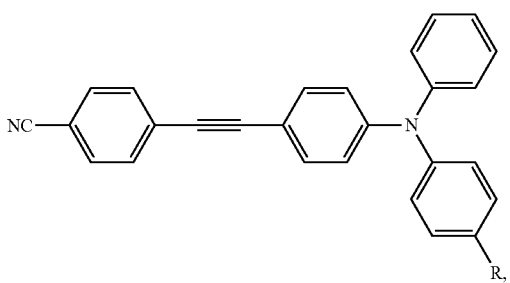

R being a substituent for covalently grafting the molecular probe to a substrate, such as a substituent functionalized with alkoxyl, halogen, thiol, sulfoxide, alkyl halides, carboxylic acid, amino alkyl, phosphate or phosphoryl groups, and combinations thereof.

According to a further embodiment, which can be combined with any other embodiment disclosed herein, the immobilized molecular probe is solvatochromic. A solvatochromic immobilized molecular probe may be rather sensitive to changes in the properties of the (adulterated) gasoline.

According to a further embodiment, which can be combined with any other embodiment disclosed herein, the immobilized molecular probe is embedded in a matrix on a substrate and/or immobilized on the substrate, such as adsorbed, ionically bonded, noncovalently bonded, and/or covalently bonded; the substrate optionally being on a test-strip or a test-strip. It is advantageous to control the immobilization of the molecular probe as it can provide for robust immobilization and reduce leaching. The immobilization may also be controlled so as to maintain significant environmental sensitivity of the molecular probe, such as sensitivity to the sample.

According to a further embodiment, which can be combined with any other embodiment disclosed herein, the substrate is selected from a group consisting of: a cellulose, an aminated cellulose, a nitrocellulose, a fabric, a glass fiber, an organic polymer, an inorganic fiber, and any combination thereof; the substrate optionally being a fiber and/or a paper. The substrate can be selected so as to enable immobilization of the molecular probe and to ensure the environmental sensitivity of the immobilized molecular probe.

According to a further embodiment, which can be combined with any other embodiment disclosed herein, the immobilized molecular probe is grafted through an amide bond to an aminated cellulose substrate. Amide bonds can be particularly stable and the immobilization is reproducible, and can maintain significant environmental sensitivity of the molecular probe.

According to a further embodiment, which can be combined with any other embodiment disclosed herein, the method also includes estimating a gasoline, ethanol, or kerosene content of the sample based on the photoluminescence. An estimation of the components of the sample is advantageous in that it can provide quantitative information to users.

According to a further embodiment, which can be combined with any other embodiment disclosed herein, the sample is contacted to the immobilized molecular probe by dipping the substrate into the sample or dropping the sample onto the substrate or spraying the substrate with the sample. Dipping, dropping, and spraying are convenient means of applying the sample to the immobilized molecular probe, and can be done by personnel without extensive training.

According to a further embodiment, which can be combined with any other embodiment disclosed herein, the method also includes determining a signal, a brightness, a brightness ratio, such as two wavelengths, a luminance, a photoluminescence quantum yield, a spectrum, and/or a photoluminescence kinetics such as a lifetime of the photoluminescence from the immobilized molecular probe in contact with the sample and/or after contact with the sample. It is advantageous to have multiple possible signal types from which to aid in greater confidence and accuracy in determining whether the photoluminescence is indicative of adulterated gasoline.

According to a further embodiment, which can be combined with any other embodiment disclosed herein, a portable device such as a smartphone, tablet, or mobile communication and computing device collects the photoluminescence and optionally determines whether the photoluminescence is indicative of adulterated gasoline; the portable device comprising optionally a lens or fiberoptic for collecting the photoluminescence. Portable devices are convenient and can be used by personnel without extensive training. A lens or optic is advantageous for providing a means to collect a signal.

According to a further embodiment, which can be combined with any other embodiment disclosed herein, the method includes exciting the immobilized molecular probe with an ultraviolet or visible light source, such as a camera flash, an LED, a laser, or an incandescent light. It is advantageous to have a light source for exciting the molecular probe.

According to a further embodiment, which can be combined with any other embodiment disclosed herein, comparing the photoluminescence to a calibration; such as comparing a signal, such as the luminescence, to a reference which may be stored data or a reference spot on test strip. A comparison can be advantageous for increasing the accuracy of the results.

Herein is disclosed a test strip for the detection of adulterated gasoline in a sample, including an immobilized molecular probe embedded in a substrate and/or immobilized to the substrate, the immobilized molecular probe having photoluminescence which is environmentally sensitive to adulterated gasoline. A test strip is convenient and can be used by personnel without extensive training.

According to a further embodiment, which can be combined with any other embodiment disclosed herein, the test strip includes a reference photoluminescence species such as for calibration of the photoluminescence of the immobilized molecular probe; the reference photoluminescence species being optionally relatively environmentally insensitive. A reference/calibration can aid in providing for accurate results.

According to a further embodiment, which can be combined with any other embodiment disclosed herein, the test strip includes multiple spots and/or lines of photoluminescent species including the immobilized molecular probe. Multiple spots and/or lines can provide greater accuracy/confidence in the results.

According to a further embodiment, which can be combined with any other embodiment disclosed herein, the test strip is covered entirely with molecular probe. This can be advantageous for providing a bright signal.

According to a further embodiment, which can be combined with any other embodiment disclosed herein, the sample is treated to remove autofluorescent species before contact with the molecular probe, such as treatment with activated charcoal.

According to a further embodiment, which can be combined with any other embodiment disclosed herein, the molecular probe is covalently attached to the substrate through a spacer group, the space group being, for example, 6 to 48 atoms in length, or 6 to 24 atoms, or 1 to 10 nm, or 1 to 5 nm. A spacer group may allow greater steric freedom of the molecular probe and may allow the sample to more easily contact the molecular probe thereby more readily influencing the environment of the molecular probe, such as the viscosity and/or polarity thereof.

DETAILED DESCRIPTION

Herein, the terms "microenvironment" and "environment" may be used interchangeably in certain contexts, particularly when referring to the "environment" of a molecular probe. Herein the term PAH can refer to polycyclic aromatic hydrocarbons. Herein, the terms "dye," and "indicator" may be used, in context, synonymously with "molecular probe" particularly when referring to a nonpolymeric photoluminescent species. A molecular probe which is grafted to a substrate, as described herein, is to be regarded as a molecular probe. Herein, "immobilized" may be used to describe a molecular probe which is associated with a substrate, such as physically adsorbed, chemically grafted, and the like. An "immobilized" molecular probe may be at least partially capable of eluting and/or desorbing when exposed to particular solvents. Herein a twisted intramolecular charge transfer state of a molecular probe can be "accessible" such as variably accessible. The rate of reconfiguration from a planar to a twisted intramolecular charge transfer state (and possibly vice versa) may be environmentally dependent, such as dependent on the local viscosity and/or polarity. Herein "DCC" refers to N,N'-dicyclohexylcarbodiimide. Herein "activated charcoal," "activated carbon," "active charcoal," and "activated carbon" are used synonymously.

Adulteration of gasoline with kerosene, for example, can result in an annual loss of sales running into multiple millions. Such adulteration can harm the environment. It is possible to detect such adulterated gasoline, but many methods require expensive and complex equipment, experts, and/or laboratory environment. A simple method that can, for example, be used on the spot, e.g. at filling stations, is desired.

Figures 1, 2:
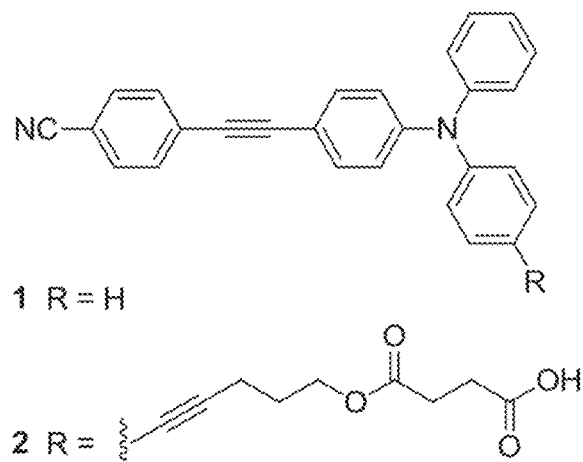
FIG. 1 illustrates, according to embodiments described herein, molecular probes 1 and 2 referred to herein, molecular probe 1 being R=H, and molecular probe 2 having the R with the terminal carboxylic acid.
FIG. 2 shows, according to embodiments described herein, some photoluminescence properties of molecular probes 1 and 2 in different environments/solvents/liquids/samples.

FIG. 1 depicts, according to embodiments described herein, molecular probes 1 and 2, which can exhibit typical photophysical properties of π-extended charge transfer dyes. Molecular probes 1 and 2 absorb in the UV-blue range and emit with high quantum yields in the blue-green range of the visible light (FIG. 1 and FIG. 2).

Molecular probes, such as those depicted in FIG. 1, can be immobilized on a substrate. Immobilized molecular probes that have photoluminescence which is environmentally sensitive can be suitable for the detection of adulterated gasoline in a sample.

Molecular probes which are environmentally sensitive to polarity are particularly contemplated. Without being bound by theory, adulteration of gasoline may change the polarity of the gasoline; for example, excess alcohol, such as ethanol, may increase the polarity of the gasoline. A molecular probe which has a polar excited state, especially an excited state that is significantly more polar than the ground state, may be rather sensitive to the presence of adulterated gasoline, particularly adulterated gasoline in which the polarity is altered due to the adulteration. For example, charge transfer dyes can be sensitive to adulterated gasoline, and can be suitable molecular probes.

According to embodiments described herein, the environmentally sensitive molecular probes 1 and 2 are suitable for a method for detecting adulteration of gasoline, particularly with kerosene or ethanol. Molecular probes 1 and 2 are examples of molecular probes with solvatochromic properties. Molecular probes 1 and 2 have a triphenylamino moiety as donor (D), phenylacetylene as conjugated linker and a cyano group as acceptor (A). Molecular probe 2 was functionalized with a carboxylic acid termination for grafting on a substrate, such as paper, particularly paper test trips. Other functionalities are contemplated. The photophysical properties of the environmentally sensitive molecular probes, especially in gasoline blends with kerosene and ethanol can be exploited for determining were studied before adsorption or grafting on test-strips. The reading on those test-strips could be achieved by a standard fluorometer, or with a portable device such as a smartphone, tablet, or mobile communication and computing device. The portable device can include suitable light excitation.

According to embodiments described herein, an environmentally sensitive molecular probe is sensitive to polarity; particularly, molecular probes which have a photoluminescence sensitive to the polarity of the environment are contemplated. According to embodiments described herein, charge transfer dyes, such as molecular probes 1 and 2 are suitable for detecting adulterated gasoline in a sample. According to embodiments described herein, the excited state of the molecular probe is more polar than the ground state, which may especially lead to sensitivity to the polarity of the environment.

FIG. 2 depicts, according to embodiments described herein, photophysical properties of molecular probes 1 and 2 in various solvents and gasoline. The similar properties of the two molecular probes indicated the negligible influence of the aryl moiety substituent for 2. Other substitutions are contemplated, particularly substitutions that allow for immobilization, such as covalent coupling, of the molecular probe to a substrate.

Molecular probes 1 and 2 also presented large Stokes shifts from 40 to 200 nm depending on the solvent. This shift was mostly due to the shift of the emission maxima from 401 to 543 nm upon increasing solvent polarity.

Figure 3:
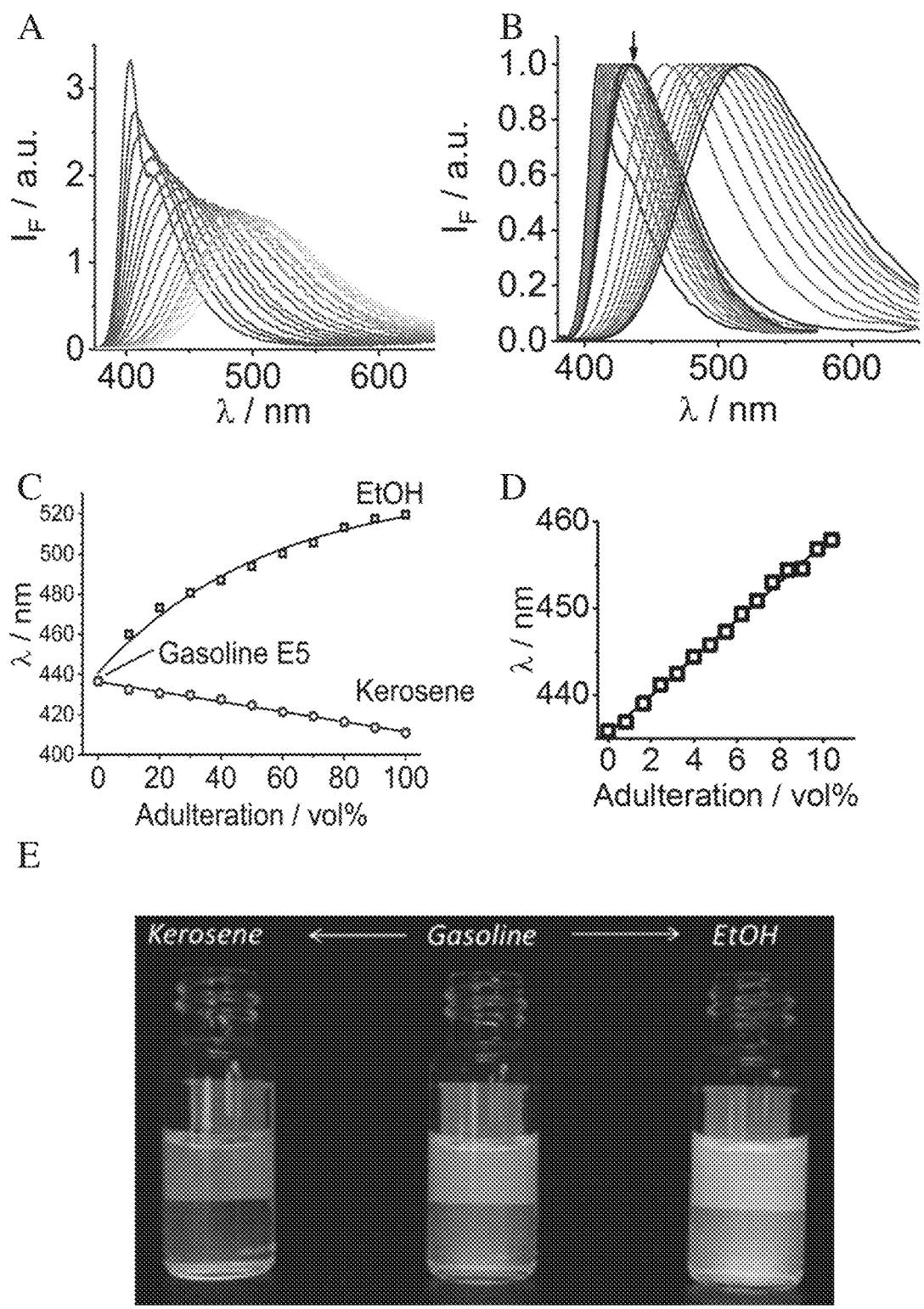
FIG. 3 illustrates, according to embodiments described herein, (A) Emission spectra of molecular probe 1 in decane-ethanol blends; (B) molecular probe 2 in gasoline-ethanol/-kerosene, with arrow signaling gasoline spectra and steps of 10 vol %; (C) Emission maxima of molecular probe 2 in gasoline-ethanol/-kerosene blends; (D) emission maxima for ethanol 0-10%; (E) Pictures of solutions of molecular probe 2 in kerosene, gasoline and ethanol upon UV excitation. ($c_1=c_2=4$ μM, $\lambda_{exc}=340$ nm).

FIG. 3(A) illustrates, according to embodiments described herein, emission spectra of molecular probe 1 in decane/ethanol blends. FIG. 3(B) illustrates, according to embodiments described herein, molecular probe 2 blends of in gasoline and ethanol or gasoline and kerosene. The arrow of FIG. 3(B) indicates the spectrum of molecular probe 2 in gasoline. Blends were prepared with steps of 10 vol %. FIG. 3(C) illustrates, according to embodiments described herein, emission maxima of molecular probe 2 in gasoline-ethanol/-kerosene blends and FIG. 3(D) illustrates, according to embodiments described herein, a linearity plot for low amounts of ethanol. FIG. 3(E) illustrates, according to embodiments described herein, pictures of solutions of molecular probe 2 in kerosene, gasoline and ethanol upon UV excitation. ($c_1 = c_2 = 4$ µM, $\lambda_{exc} = 340$ nm).

According to embodiments described herein, solvatochromatic and/or solvatokinetic molecular probes are used for the detection of gasoline adulteration.

Molecular probe 1 exhibited a resolved emission band at 403 nm in decane, which was used to approximate complex fuel mixtures without potentially interfering additives. Molecular probe 1 exhibited a broad emission band at 511 nm in ethanol. In gasoline, molecular probe 2 also showed an emission band centered at 435 nm which underwent a bathochromic shift of 86 nm ($\lambda_{em} = 521$ nm) upon increasing proportion of ethanol (see FIG. 3(B, C).

Without being bound by theory, a polar solvent shell may affect the energy of a polar excited state, including for a mainly nonpolar solvent that contains a rather low ethanol content (see FIG. 3(D)). A linear shift for ethanol 0-10 vol % can be fit (FIG. 3D) for the exemplary molecular probe 2. There can be a non-linear shift for higher proportions of ethanol, such as up to 100 vol %, as illustrated in FIG. 3(C).

It is possible to have a calibrated curve or data set for estimating (e.g. by comparison or calculation), from the collected photoluminescence upon exposure to a sample, the content of the sample, such as whether the gasoline is adulterated, and may also estimate the fraction of ethanol, kerosene, or gasoline, in the sample.

Such effects can allow assays for gasoline diluted on purpose with high amounts of ethanol and possibly more accurate monitoring of gasoline E5 directly from the refinery. As also illustrated in FIGS. 3B and 3C, increasing the proportion of kerosene can induce a hypsochromic shift, which may contrast the effect of ethanol. The hypsochromic shift due to increasing content of kerosene mixed in gasoline can be regarded as being illustrative of a decrease of the mixture polarity. For molecular probe 1, the hypsochromic shift is about 24 nm ($\lambda_{em} = 411$ nm) (FIG. 3B, C). This shift appeared to be linear over the total range of 0-100% vol. fractions of kerosene in the mixture. Limits of detection of 0.5 vol % and 5.4 vol % and limits of quantification of 1.8 vol % and 18.0 vol % were respectively calculated for ethanol and kerosene adulteration. These values match the often-encountered proportion of ethanol or kerosene found in adulterated gasoline (10-30 vol %).

According to embodiments described herein, the method includes determining a signal, a brightness, a brightness ratio, a luminance, a photoluminescence quantum yield, a spectrum, and/or a photoluminescence kinetics such as a lifetime of the photoluminescence from the immobilized molecular probe in contact with the sample and/or after contact with the sample. It is possible to use one or multiple parameters for determining whether the photoluminescence is indicative of adulterated gasoline. The photoluminescence (e.g. one or more collected signals therefrom) may allow for estimating a gasoline, ethanol, or kerosene content of the sample. A skilled person has the ability to generate calibration and/or reference data from various types of photoluminescence measurements, with respect to known mixtures of gasoline and adulterants.

Test-Strips for Gasoline Adulteration

Molecular probes 1 and 2 can also, according to embodiments described herein, be utilized in an immobilized form. Such immobilization, such as onto a solid support, can facilitate in-the-field assays. For example, environmentally sensitive molecular probes can be immobilized on filter paper or polymer matrices. Filter paper is attractive because it can be economical. Test-strips can be prepared by adsorption of at least one of molecular probes 1, 2 in 1 mM toluene solutions on filter paper. However, it is possible that not every substrate will be suitable for immobilization of the molecular probes. For example, the molecular probes on Whatman 1 (referred to as W1 herein) can possibly be inadequately immobilized, for instance, due to diffusion of the molecular probes off the substrate, such as in the case of high ethanol proportions.

According to embodiments described herein, chemically grafting the molecular probe onto the substrate can be performed. For example, molecular probe 2 was grafted on aminated Whatman 1 paper (referred to as W1-NH2 herein) by means of a DCC coupling to yield test-strips with a molecular probe concentration of 32.6 $\mu mol \cdot g^{-1}_{paper}$. Other chemical grafting chemistries are possible. Molecular probe 2, immobilized to a substrate, by DCC coupling to W1-NH2, is referred to as M1 herein.

According to embodiments described herein, a molecular probe can be covalently immobilized to the substrate; for example, by: carbodiimide driven condensation of carboxylate/amines to form amides; aldehyde-amine based couplings, sulfhydryl chemistry, isothiocyanates and amine coupling chemistry; epoxides and nucleophiles such as amines; silane chemistry; azides; nucleophilic replacement of leaving groups such as N-hydroxy succinimides by amines; maleimide sulfhydryl chemistry; diels-alder reactions; and numerous homo- and hetero-bifunctional chemical cross-linkers.

Figure 4:
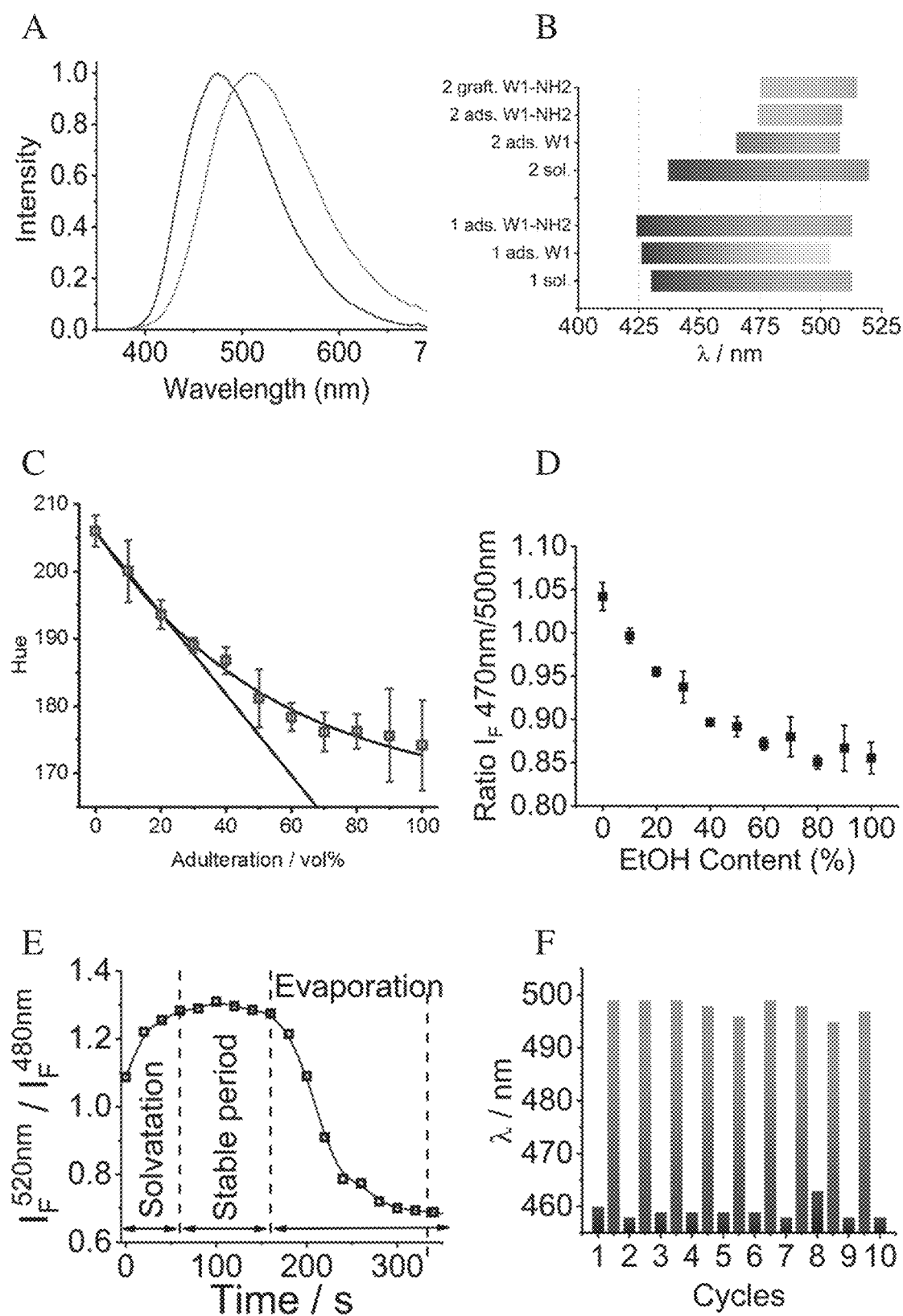
FIG. 4 illustrates, according to embodiments described herein, (A) emission spectra of molecular probes 2 in solution or immobilized in contact with gasoline and ethanol; (B) spectral dynamic ranges of molecular probes 1 and 2 in solutions or immobilized, in gasoline/ethanol blends; (C) Hue and (D) spectral shift of an immobilized molecular probe on a test-strip in various gasoline blends. (E) 520/480 nm fluorescence intensity ratio vs time of M1 test-strip wetted with 30 μL of 2:8 gasoline:EtOH blend. (F) Emission maxima of M1 test-strips after addition of 30 μL of gasoline (blue) and ethanol (green) for ten cycles ($\lambda_{exc}=340$ nm).

Contacting gasoline to a M1 test-strip led to an emission centered at 475 nm, whereas ethanol shifted the emission to 515 nm and kerosene to 472 nm (FIG. 4A). This is a decrease of the measuring range compared to molecular probes 1 and 2 in solution. Such compression of the dynamic range can be observed for both adsorbed and grafted molecular probes on substrates, such as cellulose and aminated cellulose. This may indicate an influence of the substrate on the molecular probe, e.g. influence of the aminated cellulose matrix on the immobilized molecular probe 2 (see FIG. 4B). Without being bound by theory, the environment of the molecular probe may be less sensitive to the properties of the sample, and this may be attributable to the immobilization. It is possible that the substrate impacts the polarity of an immobilized molecular probe, to a significant extent, even when the substrate (or test strip) is contacted with the sample.

FIG. 4B illustrates, according to embodiments described herein, the dynamic range of the photoluminescence of immobilized and solution phase molecular probes 1 and 2 when exposed to blends of gasoline/ethanol. In FIG. 4B, the topmost 4 bands correspond to molecular probe 2. The topmost band is immobilized molecular probe 2 grafted to a W1-NH2 substrate; the next is the adsorbed form of immobilized molecular probe 2 on W1-NH2; the next down is the adsorbed form of immobilized molecular probe 2 on W1; and the next down is solvated molecular probe 2. Of these forms of molecular probe 2, the solvated form has the greatest dynamic range. The dynamic range of the immobilized forms are shown to be suitable as environmentally sensitive probes, sensitive to adulterated gasoline. The dynamic range of molecular probe is shown in the bottom 3 bands of FIG. 4B. At the very bottom is molecular probe 1 in solvated form; the next up is molecular probe 1 adsorbed to W1, and the next up is molecular probe 1 adsorbed on W1-NH2. It is seen that the dynamic range of molecular probe 1 is not compressed as much as that of molecular probe 2 upon immobilization.

According to embodiments described herein, the molecular probe is covalently attached to the substrate through a spacer group, the space group being, for example, 6 to 48 atoms in length, or 6 to 24 atoms, or 1 to 10 nm, or 1 to 5 nm. A spacer group may allow greater steric freedom of the molecular probe and may allow the sample to more easily contact the molecular probe thereby more readily influencing the environment of the molecular probe, such as the viscosity and/or polarity thereof.

Spectral analyses of various gasoline-ethanol blends showed an increased linearity range from 0 to 20 vol % compared to the 0-10 vol % in solution (e.g. compare FIGS. 4C and 3(C) and 3(D)). Using a standard camera to take pictures of the strips and converting them to appearance parameters such as hue colors led to a linearity range up 25 vol % (FIG. 4C, D).

Determination of ethanol content in gasoline with M1 produced very good results with an average accuracy of 5% ethanol in gasoline, with limits of detection of 10%. Typical adulterations of gasoline normally are within the 10-30% range, as less than 10% may have negligible economic impact, while more than 30% is at a range where detection without instrumentation can be possible. This demonstrates that the test strip M1 is sensitive in a useful range.

According to embodiments described herein, M1 grafted to a substrate, such as by DCC coupling to a W1-NH2 substrate, can be used to determine the adulteration of gasoline with ethanol.

FIG. 4(E) illustrates, according to embodiments described herein, photoluminescence collected when the test-strip emission was measured 60 seconds after dipping in the fuel blend (FIG. 4E). The collected photoluminescence can be used to determine a ratiometric photoluminescence intensity, as shown in FIG. 4(E). FIG. 4(E) is representative of photoluminescence that can be influenced by solvation kinetics and the volatility of the analytes. A ratio of intensity such as at two different wavelengths can be used as a parameter on which to base the determination of adulteration of the gasoline, and may allow for an estimate of the content of adulterant, such as kerosene or ethanol.

According to embodiments described herein, the photoluminescence can be collected for a duration in which the photoluminescence is relatively stable, such as after a period of solvation, or after a period while the sample reaches the molecular probe's environment, such as by diffusion and/or capillary action or the like. The relatively stable period may precede a period of relative instability, such as a period of evaporation of the sample. Without being bound by theory, as can be understood from FIG. 4(E), during the first minute, solvation of the grafted molecular probe can take place, producing a gradual fluorescence wavelength shift (or transport of the liquid sample to the molecular probe's environment). The photoluminescence may subsequently stabilize. For example, emission from the strip could be measured at 60 to 160 seconds ensuring accurate determination of the blend proportions. Alternatively/additionally, an average photoluminescence can be determined that is calculated, determined, collected, and/or selected from an appropriate duration of (dynamic) photoluminescence, such as from an algorithmically determined set of data from dynamically recorded photoluminescence data. A set of maximal or minimal parameters (intensity, intensity ratio, or the like) of collected photoluminescence data may serve as the photoluminescence that is used to determine whether the photoluminescence is indicative of adulterated gasoline.

Referring again to FIG. 4(E), after a relatively stable period, the signal may change or become unstable again, such as due to evaporation of higher vapor pressure components. This may result in a color shift back to the dry strip wavelength.

It may be possible to use a test strip repeatedly, particularly when the molecular probe is stably immobilized to the substrate. For example, a M1 test-strip was used for 10 successive measurements alternatively by wetting in gasoline and ethanol with a washing and drying step with hot air for 10 seconds in between. Negligible leaking of the molecular probe was observed and the optical response of the material remained stable over the measurements (FIG. 4(F)).

According to embodiments described herein, the test-strip is reusable, particularly an M1 test-strip in which the molecular probe is covalently immobilized to the substrate.

Figure 5:
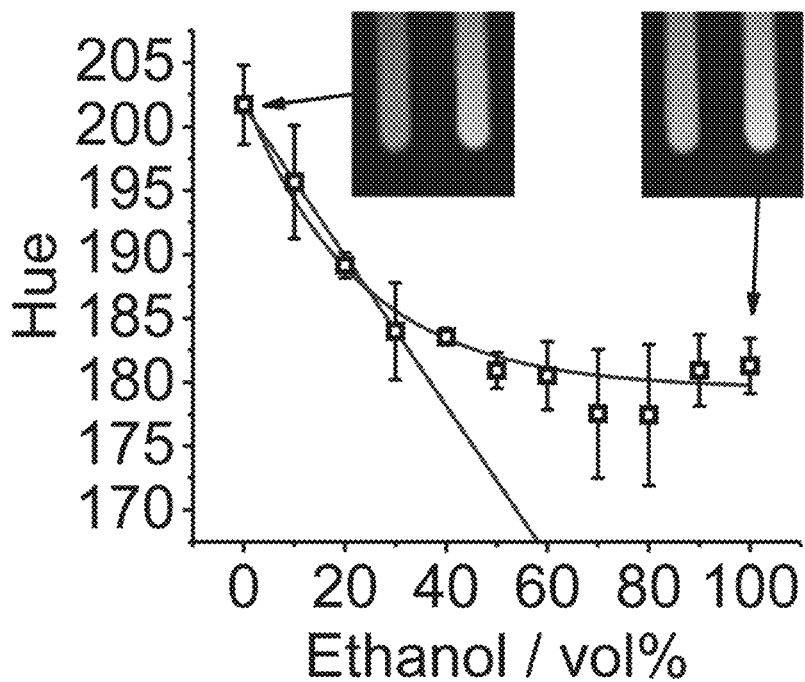
FIG. 5 illustrates, according to embodiments described herein, measured hue values of an M1 test-strip, having been dipped in gasoline-ethanol blends.

FIG. 5 illustrates, according to embodiments described herein, photoluminescence of a M1 test-strip in ethanol/gasoline blends. Photoluminescence can be determined and/or quantified using appearance parameters such as hue values, for example. A digital camera, which may be integrated into a portable device such as a smartphone, tablet, or mobile communication and computing device, may collect the photoluminescence. Hue values may be determined using data of a digital image.

For example, after dipping the test strip into a gasoline sample (or spotting the sample on the strip), a photograph of a reference and test strip can be taken. Software may average the RGB values of the pixels in predefined spatial areas, such as those corresponding to the position of the strips, and/or position of the immobilized molecular probe and/or reference. Collected photoluminescence can be converted to appearance parameters such as hue values for numerical analysis. Alternatively/additionally, a test strip may include multiple photoluminescent species, so that a reference is provided on the test strip. The test strip may include multipole spots, lines, or the like.

A system, which can include a portable device such as a smartphone, tablet, or mobile communication and computing device, can be calibrated, such as internally, for qualitative measurements. According to embodiments described herein, a multiple point calibration procedure such as with reference solutions (such as gasoline and ethanol) can be performed providing quantitative results (see FIG. 5, for example). Reference and/or calibration parameters can be stored, such as in memory of the portable device and/or can be available remotely. Data can be transmitted so that algorithms and the like can be performed on the data, and/or the data can be compared to the reference and/or calibration. An internal file can be available on the portable device for reference and/or calibration. Alternatively/additionally, the device may run algorithms for determining whether the photoluminescence is indicative of adulterated gasoline.

For example, image processing and data analysis can be carried out with a smartphone application, such as an Android custom application. As an example, a calibration curve can be one obtained using the photoluminescence collected by the camera of a portable device, such as a digital camera. Tests indicate that detection can be within 5% vol error for proportions of ethanol between 10-30% vol.

Smartphones can be used to perform the method, for example. Measurement systems using smartphones or another mobile communication device are suitable for on-site testing by unskilled personnel. Results and/or data can be transmitted remotely, from/to the device. For example, the data can be transmitted from the device so that the data can possibly be accessed by others.

According to embodiments described herein, an excitation source and a controlled dark chamber may be used, particularly in combination with the portable device such as the table, smartphone, or mobile communication and computing device. For example, an ultraviolet or visible light source, such as a camera flash, an LED, a laser, or an incandescent light can be used.

Figure 6:
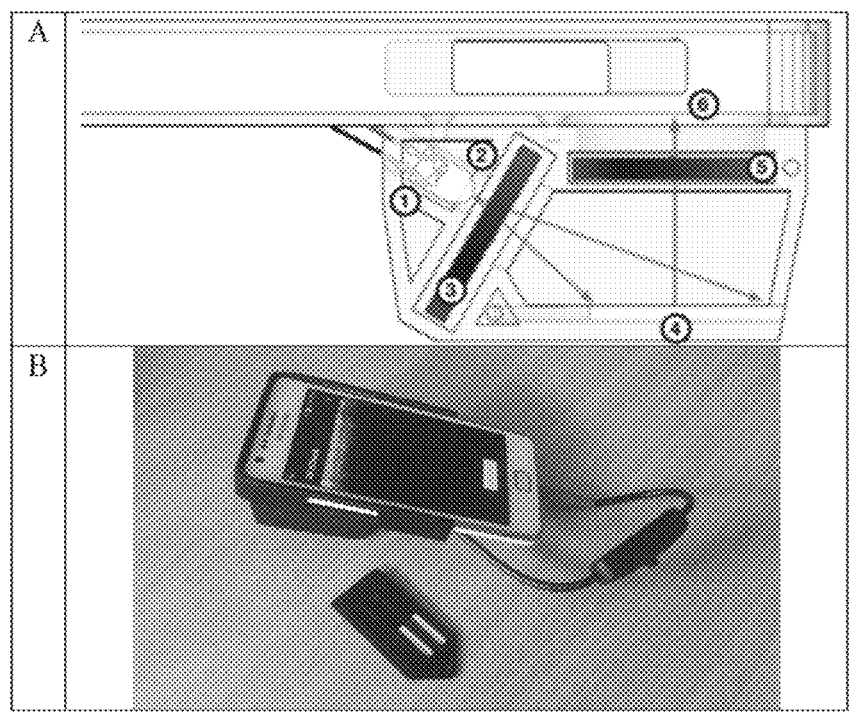
FIG. 6 illustrates, according to embodiments described herein, (A) schematic of an integrated smartphone and case. (B) Picture of the smartphone measurement system.

FIG. 6 illustrates, according to embodiments described herein, a portable electronic device for performing the method. As an example, a smartphone measurement system capable of analyzing the fluorescence wavelength shift response of M1 test-strips based on a consumer smartphone is hereby disclosed. Optics elements may include the camera of a smartphone or digital camera, and may also include optical filters and an excitation source, for example. For example, a 3D printed smartphone case combined with a dark chamber (approximately 20×30×40 mm, for example) can be used. FIG. 6 shows an LED 1, diffuser 2, optical filter 3, test strip 4, optical filter 5, camera 6.

In an embodiment, the excitation of the test-strips was achieved with a UV-LED at 365 nm driven by 20 mA DC current, drawn from the smartphone battery via an USB on-the-go (OTG) connection. The excitation light is arranged to illuminate the test strip(s) and/or reference strip(s) at an angle of around 60°. A detector such as a CCD or CMOS, particularly within a smartphone or tablet, is often insensitive to UV, so it may be that no special filtering of the collected light is required. Test strips and/or reference strips were placed in a holder, beside a paper strip coated with styrene as reference, and photoluminescence was collected and/or measured with the smartphone CMOS camera.

A simple and powerful analytical tool is disclosed based on charge transfer dyes used as molecular probes, according to embodiments described herein. For example, molecular probes were synthesized and characterized before being grafted on aminated cellulose paper to afford test-strips for detection of gasoline adulteration with ethanol or kerosene. The molecular probes appeared to be efficient fluorescent purity indicators of gasoline either for lighter alkanes such as kerosene or for polar solvent like ethanol with respective limits of detection of 5.4% and 0.5% vol for the potential adulterants.

Test strips prepared with molecular probes can give a clear and selective fluorometric response in presence of polar adulterant like ethanol with an error of 5% vol and a large range of adulteration (0-30% vol.). Integration of the rapid test in an embedded smartphone based setup led to similar results, allowing measurement on-site. The smartphone setup integrated an UV-LED as excitation source and software performing the analysis. The error margins and dynamic ranges were suitable for detecting adulterants at levels often found in the field. The high accuracy of the method for ethanol adulteration could allow the monitoring of refined gasoline.

FURTHER DETAILS AS EXEMPLARY EMBODIMENTS

Materials, Methods and Instrumentation

Kerosene was commercially available at Aldrich and gasoline (E5 grade) was obtained from a gas station at Berlin-Adlershof in January 2016. Since gasoline can be autofluorescent due to the possible presence of fluorescent polycyclic aromatic hydrocarbons or even marker dyes, a pretreatment with active charcoal was optionally performed. This pre-treatment followed either a laboratory-based protocol in which 10 wt % of active charcoal was suspended in fresh blends, stirred for 1 h, centrifuged and filtered to remove the charcoal, or an embedded-based protocol using a stainless steel in-line filter holder (47 mm, PALL) with active carbon paper filters (typically 4).

Reagents for synthetic procedures were obtained from commercial suppliers and used without further purification, unless indicated. Air- and moisture-sensitive reactions were carried out with previously dried materials under $N_2$ atmosphere. TLC experiments were performed over Merck Silica Gel 60 $F_{254}$ TLC. Reactions were monitored using a 254 nm hand-held lamp. Column chromatography was carried out with Merck Silica gel 60 (0.040-0.063 mm). NMR spectra were recorded on a 500 MHz (100.6 MHz for $^{13}C$) Bruker AV 400 spectrometer at 300 K using residual protonated solvent signals as internal standard ($^1H$: δ ($CDCl_3$)=7.26 ppm and $^{13}C$: δ ($CDCl_3$)=77.16 ppm). Assignments are based on chemical shifts. Mass spectra were measured on a Waters LCT Premier XE.

UV-vis absorption spectra were recorded on a Specord 210-Plus spectrophotometer from Analytik Jena. Steady-state fluorescence measurements were carried out on a FluoroMax-4 spectrofluorometer from Horiba Jobin-Yvon, using standard 10 mm path length quartz cells. All the solvents employed for the spectroscopic measurements were of UV spectroscopic grade (Aldrich).

Fluorescence signal of the test-strip was monitored using a home-made setup combining a USB spectrometer and a commercial camera. A UV light source emitting at $\lambda_{em}$=365 nm was used to excite the fluorophore grafted to the paper strip. The fluorescence was directly collected by a glass fiber placed below the strip coupled to an Ocean Optics USB2000+ spectrometer. Additionally, a Canon Powershot S90 digital camera was placed in a front face position to take pictures of the strips. Parameters were adjusted to average the 60 Hz blinking of the UV light source (f/3.5, speed 1/40, ISO1250, custom white balance). Finally, pictures were treated numerically to extract the Hue coordinates of the emitted fluorescence.

Procedures 4-((4-(diphenylamino)phenyl)ethynyl)benzonitrile 1

Compound 1 was synthesized according a reported protocol with a 63% yield.

4-bromo-N-(4-ethynylphenyl)-N-phenylaniline 3. 1 g (2.5 mmol) of 4,4'-dibromotriphenylamine and 346 µL (2.5 mmol) of ethynyltrimethylsilane were dissolved in a 20 mL mixture of dry THF and $Et_3N$ 1:1 v/v. The solution was deoxygenated by sparkling Ar(g) for 10 minutes. After that time, 87 mg of bis(triphenylphosphine)palladium(II) dichloride (0.125 mmol) and 47 mg cupper iodide (0.25 mmol) were added to the mixture and the reaction was heated for 3 hr. at 50° C., then was increased to 80° C. and kept overnight. After that time, the mixture was allowed to cool down, saturated $NH_4Cl$ solution was added, and the products were extracted three times using $CH_2Cl_2$. The organic layer was washed with a saturated NaCl solution and dried with $Na_2SO_4$. 456 mg of an oily mixture were obtained. Consequently, 400 mg (0.98 mmol) of this product and 817 mg (5.9 mmol) of potassium carbonate were mixed in a 20 mL mixture of $CH_2Cl_2$ and MeOH 1:1 v/v. The reaction was kept for 1 hr. After that time, saturated $NH_4Cl$ solution was added, and the products were extracted three times using $CH_2Cl_2$. The organic layer was washed with a saturated NaCl solution and dried with $Na_2SO_4$. A column chromatography (PET:$CH_2Cl_2$, 95:5 v/v) yielded 232 mg (30%) of the desired product 3 after two steps. $^1H$ NMR (400 MHz, Chloroform-d) δ 7.37-7.31 (m, 4H), 7.30-7.23 (m, 3H), 7.10-7.04 (m, 3H), 6.95 (d, J=8.7 Hz, 4H), 3.01 (s, 1H). $^{13}C$ NMR (101 MHz, $CDCl_3$) δ 147.84, 146.70, 146.31, 133.17, 132.38, 129.55, 126.01, 125.12, 122.45, 115.92, 115.52, 83.69, 83.67. HR-MS (ESI+): m/z calculated for $C_{20}H_{15}BrN$ $[M+H]^+$: 348.0388, found: 348.0397.

4-((4-((4-bromophenyl)(phenyl)amino)phenyl)ethynyl)benzonitrile 4

127 mg (0.55 mmol) of 4-iodobenzonitrile was dissolved in a 5 mL mixture of dry THF and $Et_3N$ 1:1 v/v. The solution was deoxygenated by sparkling argon for 10 minutes. After that time, 20 mg of bis(triphenylphosphine)palladium(II) dichloride (28 µmol) and 10 mg cupper iodide (56 µmol) were added to the mixture, followed by 200 mg (0.57 mmol) of 3. The reaction was kept at room temperature overnight. Saturated $NH_4Cl$ solution was then added, and the products were extracted three times using DCM. The organic layer was washed with a saturated NaCl solution and dried with $Na_2SO_4$. A column chromatography (PET:$CH_2Cl_2$, 8:2 v/v) yielded 167 mg (65%) of the desired product 4. $^1H$ NMR (400 MHz, Chloroform-d) δ 7.62 (d, J=8.7 Hz, 2H), 7.57 (d, J=8.8 Hz, 2H), 7.41-7.35 (m, 4H), 7.30 (dd, J=8.7, 7.3 Hz, 2H), 7.14-7.08 (m, 3H), 7.03-6.97 (m, 4H). $^{13}C$ NMR (101 MHz, $CDCl_3$) δ 148.19, 146.53, 146.12, 132.88, 132.47, 131.99, 131.84, 129.62, 128.54, 126.27, 125.33, 124.33, 122.15, 118.57, 116.26, 115.26, 111.08, 94.18, 87.37. HR-MS (ESI+): m/z calculated for $C_{27}H_{18}BrN_2$ $[M+H]^+$: 449.0653, found: 449.0643.

4-((4-((4-(5-hydroxypent-1-yn-1-yl)phenyl)(phenyl)amino)phenyl)ethynyl)benzonitrile 5

100 mg (0.22 mmol) of 4 and was dissolved in a 5 mL mixture of dry THF and $Et_3N$ 1:1 v/v. The solution was deoxygenated by sparkling argon for 10 minutes. After that time, 15 mg of bis(triphenylphosphine)palladium(II) dichloride (22 µmol) and 8 mg cupper iodide (44 µmol) were added to the mixture and the reaction. Then, 30 µl (0.33 mmol) of 4-pentyn-1-ol was added and the mixture was heated for overnight at 70° C. After that time, the mixture was cooled down and the mixture was filtered through Celite and then saturated $NH_4Cl$ solution was added. The products were extracted three times using $CH_2Cl_2$. The organic layer was washed with a saturated NaCl solution and dried with $Na_2SO_4$. An isocratic column chromatography (cyclohexane:EtOAc, 8:2 to 7:3 v/v) yielded 78 mg (78%) of the desired product 5. $^1H$ NMR (500 MHz, Chloroform-d) δ 7.55 (d, J=8.4 Hz, 2H), 7.50 (d, J=8.3 Hz, 2H), 7.31 (d, J=8.7 Hz, 2H), 7.26-7.19 (m, 4H), 7.04 (dd, J=6.2, 2.7 Hz, 3H), 6.94 (dd, J=8.7, 2.8 Hz, 4H), 3.76 (t, J=6.1 Hz, 2H), 2.47 (t, J=7.0 Hz, 2H), 1.79 (p, J=6.5 Hz, 2H). $^{13}C$ NMR (126 MHz, CDCl3) δ 148.21, 146.56, 146.44, 132.85, 132.66, 132.01, 131.85, 129.58, 128.59, 125.52, 124.31, 124.07, 122.45, 118.63, 118.43, 115.25, 111.05, 94.27, 88.29, 87.36, 80.88, 61.92, 31.45, 16.09. HR-MS (ESI+): m/z calculated for C32H25N2O $[M+H]^+$: 453.1967, found: 453.1975.

4-((5-(4-((4-((4-cyanophenyl)ethynyl)phenyl)(phenyl)amino)phenyl)pent-4-yn-1-yl)oxy)-4-oxobutanoic acid 2

20 mg of 5 (44 µmol), 0.53 mg of 4-dimethylaminopyridine (4.4 µmol), 5 mg of succinic anhydride (53 µmol) were dissolved in 1.6 mL of $CH_2Cl_2$. To this mixture, 3.2 µL of $Et_3N$ (53 µmol) were added, and the reaction was kept overnight at room temperature. Then, 1 mL of water was added, and pH was adjusted to 2 with AcOH. The mixture was washed two times with water and a saturated NaCl solution. Next, it was purified using column chromatography (PET:EtOAc 3:7 v/v) yielding 21 mg (86%) of the desired molecular probe 2. $^1H$ NMR (500 MHz, Chloroform-d) δ 7.54 (d, J=8.3 Hz, 2H), 7.49 (d, J=8.4 Hz, 2H), 7.31 (d, J=8.7 Hz, 2H), 7.24-7.19 (m, 4H), 7.06-7.00 (m, 3H), 6.93 (dd, J=8.7, 4.2 Hz, 4H), 4.19 (t, J=6.3 Hz, 2H), 2.64-2.55 (m, 4H), 2.43 (t, J=7.0 Hz, 2H), 1.86 (p, J=6.7 Hz, 2H). $^{13}C$ NMR (126 MHz, $CDCl_3$) δ 176.93, 172.07, 148.18, 146.54, 146.45, 132.84, 132.68, 132.00, 131.84, 129.57, 128.57, 125.51, 124.30, 124.03, 122.44, 118.60, 118.33, 115.24, 111.02, 94.26, 88.16, 87.36, 81.04, 63.60, 28.87, 28.74, 27.80, 16.18. HR-MS (ESI+): m/z calculated for $C_{36}H_{29}N_2O_4$ $[M+H]^+$: 553.2127, found: –

Preparation of Paper Strips Grafted with Molecular Probe 2

Whatman 1 paper filter (1×4 cm, 20 pieces) were added to a 100 mL toluene solution containing 2.5 mL of APTES and the mixture was agitated at 90° C. for 24 h. After that time, the strips were washed thoroughly with EtOH, were dried and then, 10 mL of a $4·10^{-4}$ M solution of molecular probe 2 in $CH_2Cl_2$ and 0.82 mg (4 µmol) of DCC were mixed together for 30 minutes. After that time, 280 mg of aminated Whatman paper 1 and 0.55 µL of $Et_3N$ (4 µmol) were added to the mixture, and the reaction was kept for two extra hours. The paper was washed several times with $CH_2Cl_2$ and then with EtOH and allowed to dry. Differential absorption analysis of the initial solution and final solutions, together with the washing fractions, determined that the molecular probe was grafted to the paper at a concentration of 32.6 $µmol·g^{-1}_{paper}$.

Synthesis

Figure 7:
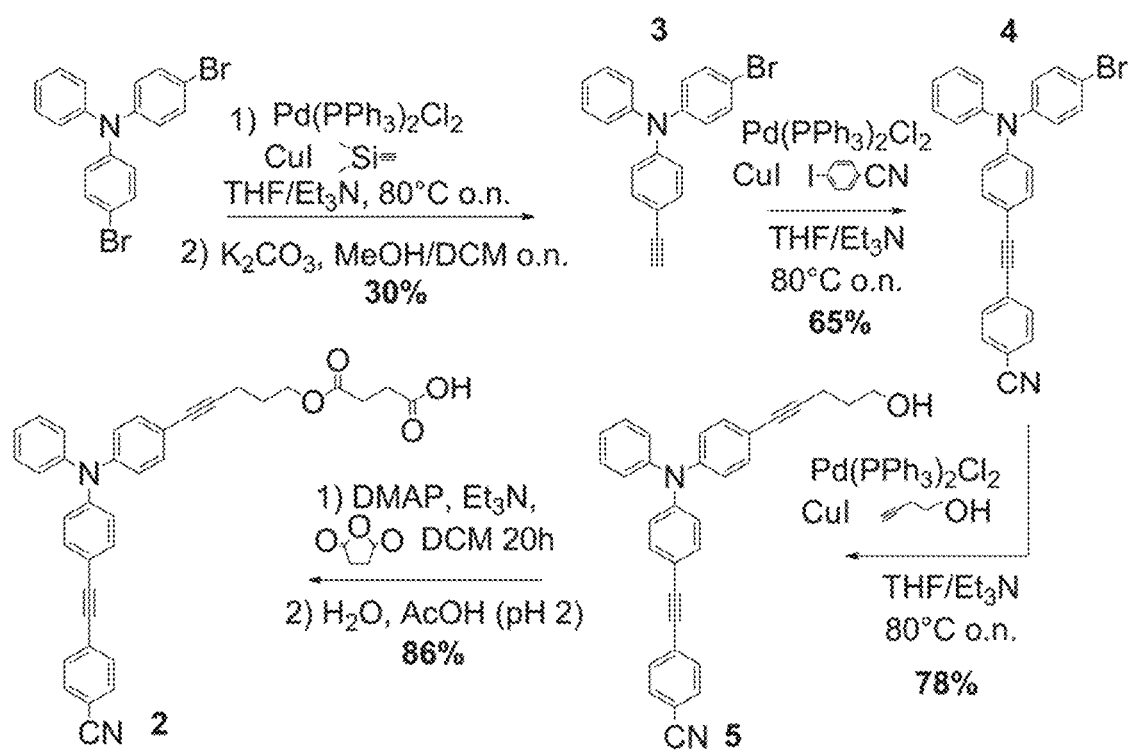
FIG. 7 illustrates, according to embodiments described herein, a synthetic scheme for a molecular probe.

With reference to FIG. 7, the following synthesis scheme of the molecular probe 2 is disclosed. Molecular probe 1 was prepared following a linear synthesis previously reported procedure from Piao et al. (Piao, M. J.; Chajara, K.; Yoon, S. J.; Kim, H. M.; Jeon, S.-J.; Kim, T.-H.; Song, K.; Asselberghs, I.; Persoons, A.; Clays, K.; Cho, B. R., First hyperpolarizabilities of hexa(ethynyl)benzene derivatives: effect of conjugation length. Journal of Materials Chemistry 2006, 16 (23), 2273-2281) and the others were prepared following an adaptation of this synthesis starting from dibrominated phenylamine (see FIG. 7). First, 4,4'-dibromotriphenylamine was coupled with trimethylsilaneacetylene using $Pd(PPh_3)_2Cl_2$, CuI and $THF/Et_3N$ as solvent mixture at 80° C. in a Sonogashira coupling reaction. The mono-functionalized product 3 was separated from the statistical distribution mixture of products and was deprotected with using potassium carbonate in $MeOH/CH_2Cl_2$ mixture. Then, 3 was coupled then with 4-iodobenzonitrile in a Sonogashira coupling reaction, to produce 4 in a 65% yield. This compound was again submitted to a Sonogashira coupling reaction, this time using 4-pentyn-1-ol to obtain 5, which underwent an esterification reaction with succinic anhydride and DMAP to form molecular probe 2 with an overall yield of 13%.

Figure 8:
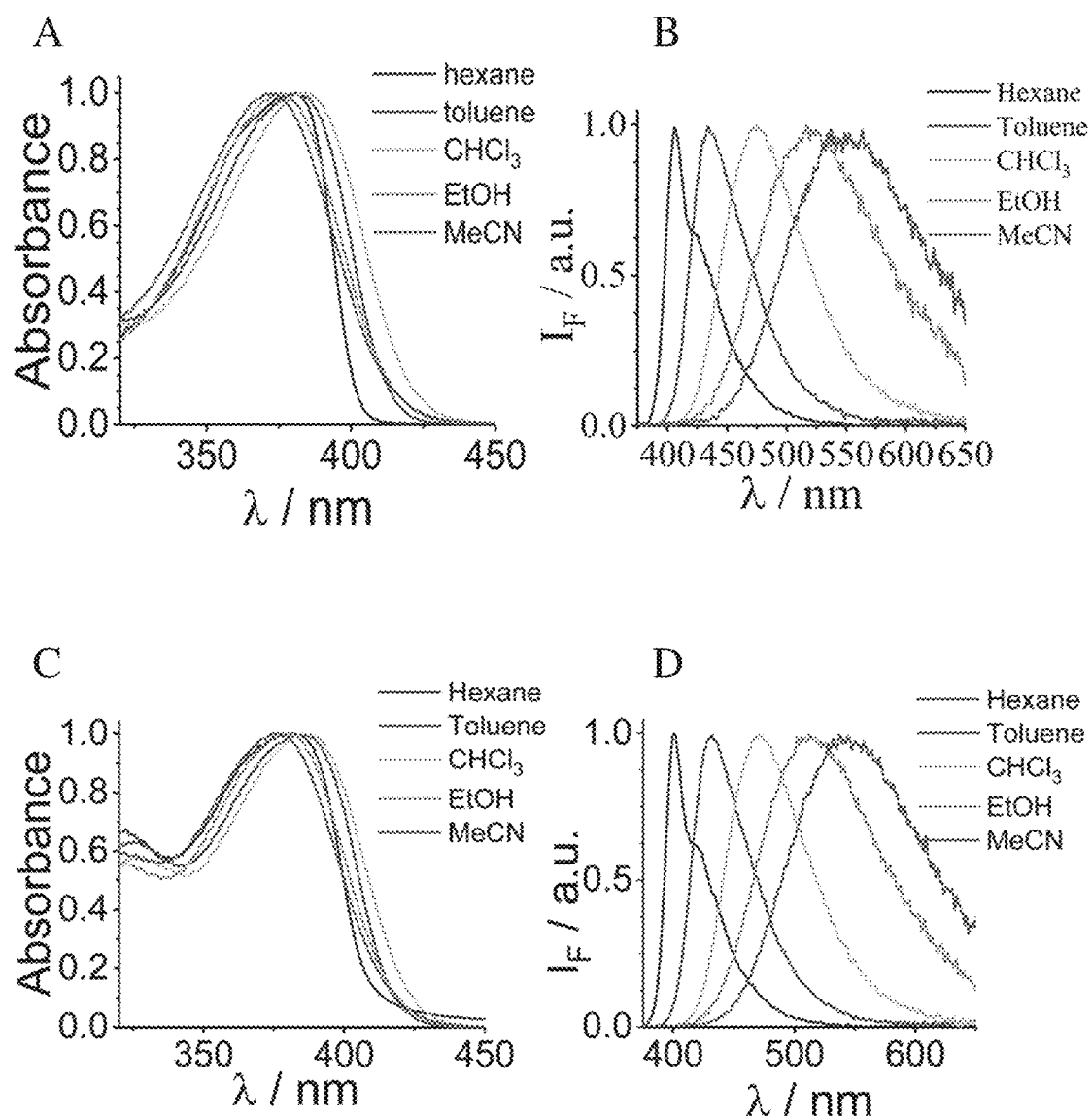
FIG. 8 illustrates, according to embodiments described herein, normalized absorption and emission spectra of molecular probe 1 (A) and molecular probe 2 (B) in various solvents ($c_1=c_2=4$ μM, $\lambda_{exc}=340$ nm).

FIG. 8 illustrates, according to embodiments described herein, normalized absorption and emission spectra of 1 and 2 in various solvents. FIG. 8(A) shows molecular probe 1 and FIG. 8(B) shows molecular probe 2. Concentration is 4 µM and excitation is at 340 nm.

Using the Lippert-Mataga equation (Equation 1), slope values proportional to the cavity size and the polarity of the excited states ($[\Delta\mu]^2/a^3$) can be calculated.

Equation 1

$$v_a - v_b = \frac{2}{hca^3}(\mu_e - \mu_g)^2 \Delta f + C \quad (1.1)$$

$$\Delta f = \frac{\varepsilon - 1}{2\varepsilon + 1} - \frac{n^2 - 1}{2n^2 + 1}. \quad (1.2)$$

(1.1) Lippert-Mataga equation and (1.2) orientation polarizability
in which $v_a$ and $v_g$ are the absorption and emission maxima in wavenumbers, h is Planck's constant, c is the light velocity, a the radius of the cavity, $\mu_e$ and $\mu_g$ the respective excited and ground state dipole moments and Δf is the orientation polarizability calculated by equation 1.2 in which Γ is the static dielectric constant and n the optical refractive index of the solvent.

Figure 9:
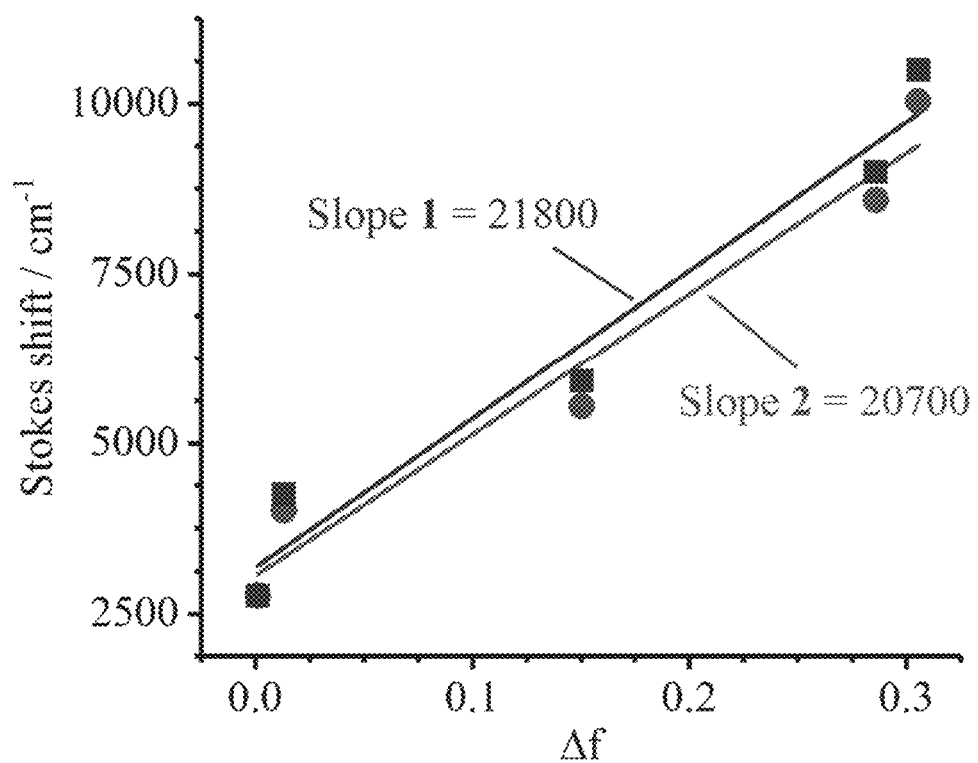
FIG. 9 illustrates, according to embodiments described herein, Lippert-Mataga correlations for molecular probes 1.

FIG. 9 illustrates, according to embodiments described herein, Lippert-Mataga correlations for molecular probes 1 and 2. With reference to equations (1.1) and (1.2), a large slope, particularly for a given size molecular probe, can indicate a substantial difference between the polarization of the ground and excited states, such as an increase of polarity in the excited state (FIG. 9). This pronounced solvatochromic behavior, especially due to a shift of the emission, observed for molecular probes 1 and 2 confirmed the possible application for polarity sensing.

The polarity differences between the solvents seemed not to have too much influence on the molecular probes' quantum yields of fluorescence. While, for this family of molecular probes, polar solvents can potentially promote strong intramolecular charge transfer and non-radiative deactivation pathways, here, only in acetonitrile the quantum yield were lower, respectively 58% and 37% for molecular probes 1 and 2. Furthermore, for obtaining a solvatochromic molecular probe for gasoline adulteration with kerosene or ethanol, response analyses can be simplified due to similar quantum yields of almost 80% for molecular probe 1 and 60-70% for molecular probe 2 in those media.

Molecular probes which include a triphenylamino moiety as a donor, and a cyano group as an acceptor, particularly those shown in FIG. 1 and immobilized forms thereof, are particularly advantageous for the present invention. These molecular probes can exhibit a relatively strong fluorescence across environments of fairly widely varying polarity. Moreover, the molecular probes suggested in FIG. 1 and immobilized forms thereof can emit across a broad region of the spectrum with a relatively high fluorescence quantum yield, a technical effect that is difficult to predict, which leads to a sensitive and bright chromatic shift which can depend on polarity.

The invention disclosed herein can offer the possibility of an immediate, accurate measurement and analysis on the spot with, for example, a portable colorimeter and/or fluorometer. The embedding of the indicator dyes into a test strip facilitates the analysis procedure so that untrained personnel can also carry out the measurements.

The present invention has been explained with reference to various illustrative embodiments and examples. These embodiments and examples are not intended to restrict the scope of the invention, which is defined by the claims and their equivalents. As is apparent to one skilled in the art, the embodiments described herein can be implemented in various ways without departing from the scope of what is invented. Various features, aspects, and functions described in the embodiments can be combined with other embodiments.

The invention claimed is:

1. A method for the detection of adulterated gasoline in a sample, the method comprising:
contacting the sample with an immobilized molecular probe, the immobilized molecular probe having a photoluminescence which is environmentally sensitive;
collecting the photoluminescence from the immobilized molecular probe;
determining whether the photoluminescence is indicative of adulterated gasoline,
wherein the immobilized molecular probe comprises a donor and an acceptor which are covalently bound to each other, and wherein the immobilized molecular probe includes a triphenylamino moiety as the donor and a cyano group as the acceptor according to the formula,

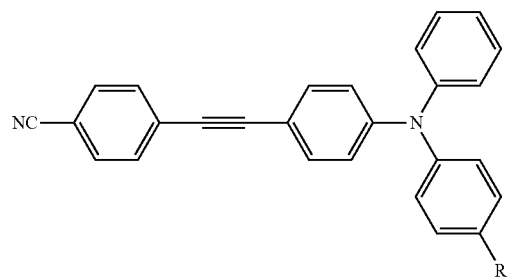

wherein R is selected from H,

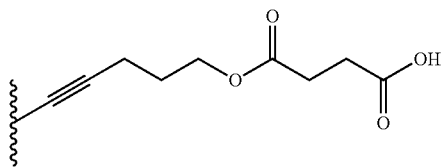 [SMILES: *C#CCCCOC(=O)CCC(=O)O]

and a species immobilizing the immobilized molecular probe to a substrate.

2. The method of claim 1, wherein the immobilized molecular probe is environmentally sensitive to polarity.

3. The method of claim 1, wherein the immobilized molecular probe has a polar excited state, the immobilized molecular probe being a charge transfer dye.

4. The method of claim 1, wherein the immobilized molecular probe is covalently immobilized to the substrate, the molecular probe covalently bound to the substrate through a spacer group.

5. The method of claim 1, wherein R includes a functional group resulting from the covalent immobilization of a molecular probe which includes a functional group for immobilizing the molecular probe; and
the immobilized molecular probe includes a spacer group for reducing the interaction of the substrate with the molecular probe.

6. The method according to claim 1, wherein the immobilized molecular probe is solvatochromic.

7. The method of claim 1, wherein the immobilized molecular probe is embedded in a matrix on the substrate and/or immobilized on the substrate; the substrate being on a test-strip or a test-strip, and wherein the substrate is selected from the group consisting of: a cellulose, an aminated cellulose, a nitrocellulose, a fabric, a glass fiber, an organic polymer, an inorganic fiber, and any combination thereof; the substrate being a fiber and/or a paper.

8. The method of claim 1, wherein the immobilized molecular probe is grafted through an amide bond to the substrate, wherein the substrate is an aminated cellulose substrate.

9. The method of claim 1, further comprising
estimating a gasoline, ethanol, or kerosene content of the sample based on the photoluminescence.

10. The method of claim 1, wherein the sample is contacted to the immobilized molecular probe by dipping the substrate into the sample or dropping the sample onto the substrate or spraying the substrate with the sample.

11. The method of claim 1, further comprising determining a signal, a brightness, a brightness ratio, a luminance, a photoluminescence quantum yield, a spectrum, and/or a photoluminescence kinetics from the immobilized molecular probe in contact with the sample and/or after contact with the sample.

12. The method of claim 1, wherein a portable device selected from a smartphone, digital camera, tablet, or mobile communication and computing device collects the photoluminescence and determines whether the photoluminescence is indicative of adulterated gasoline; the portable device comprising a lens or fiberoptic for collecting the photoluminescence.

13. The method of claim 1, further comprising exciting the immobilized molecular probe with an ultraviolet or visible light source, and comparing the photoluminescence to a calibration.

14. The method of claim 1, wherein the immobilized molecular probe is formed from a molecular probe which includes a functional group for covalently immobilizing the molecular probe to the substrate; the immobilized molecular probe includes a spacer group for reducing the interaction of the substrate with the molecular probe.

* * * * *